(12) United States Patent
Landau et al.

(10) Patent No.: US 7,238,167 B2
(45) Date of Patent: *Jul. 3, 2007

(54) NEEDLE-FREE INJECTION SYSTEM

(75) Inventors: Sergio Landau, Laguna Niguel, CA (US); Daniel E. Williamson, Sherwood, OR (US); John R. Marshall, Beaverton, OR (US)

(73) Assignee: Bioject Inc., Tualatin, OR (US)

( * ) Notice: Subject to any disclaimer, the term of this patent is extended or adjusted under 35 U.S.C. 154(b) by 211 days.

This patent is subject to a terminal disclaimer.

(21) Appl. No.: 10/756,945

(22) Filed: Jan. 13, 2004

(65) Prior Publication Data

US 2004/0199106 A1 Oct. 7, 2004

Related U.S. Application Data

(63) Continuation-in-part of application No. 10/164,920, filed on Jun. 4, 2002, now Pat. No. 6,676,630.

(51) Int. Cl.
*A61M 5/30* (2006.01)
*A61B 17/00* (2006.01)

(52) U.S. Cl. .......................... 604/70; 606/116; 604/68

(58) Field of Classification Search ........ 606/116–117; 222/129, 135, 137, 82; 128/DIG. 6; 81/9.22; 604/68, 70, 140, 141, 181, 187
See application file for complete search history.

(56) References Cited

U.S. PATENT DOCUMENTS

| | | | |
|---|---|---|---|
| 2,653,604 A | 9/1953 | Hein, Jr. | |
| 2,655,604 A | 10/1953 | Hutter | |
| 2,680,439 A | 6/1954 | Sutermeister | |
| 3,057,349 A | 10/1962 | Ismach | |
| 3,115,133 A | 12/1963 | Morando | |
| 3,202,151 A | 8/1965 | Kath | |
| 3,292,621 A | 12/1966 | Banker | |
| 3,425,413 A | 2/1969 | Stephens | |
| 3,507,276 A | 4/1970 | Burgess | |
| 3,561,443 A | 2/1971 | Banker | |
| 3,688,765 A | 9/1972 | Gasaway | |
| 3,714,943 A | 2/1973 | Yanof et al. | |
| 3,788,315 A | 1/1974 | Laurens | |
| 3,859,996 A * | 1/1975 | Mizzy et al. | 604/70 |
| 3,908,651 A | 9/1975 | Fudge | |
| 3,945,379 A | 3/1976 | Pritz et al. | |
| 4,124,024 A | 11/1978 | Schwebel et al. | |
| 4,266,541 A | 5/1981 | Landau | |
| 4,342,310 A | 8/1982 | Lindmayer et al. | |
| D277,506 S | 2/1985 | Ibis | |
| 4,592,742 A | 6/1986 | Landau | |
| 4,596,556 A | 6/1986 | Morrow et al. | |
| 4,623,332 A | 11/1986 | Lindmayer et al. | |

(Continued)

*Primary Examiner*—Kevin C. Sirmons
*Assistant Examiner*—Benjamin Huh
(74) *Attorney, Agent, or Firm*—Kolisch Hartwell, P.C.

(57) ABSTRACT

A needle-free injection device is described. The injection device includes a user-grippable housing and a syringe assembly movably secured to the housing. The syringe assembly is configured to expel injectable fluid out of a nozzle upon application of pressurized gas to the syringe assembly. The injection device also includes a pressurized gas delivery mechanism disposed within the housing and configured to selectively apply pressurized gas to the syringe assembly. The pressurized gas delivery mechanism is at least partly actuated by pressing the nozzle onto an injection site so that the syringe assembly moves relative to the housing.

20 Claims, 11 Drawing Sheets

U.S. PATENT DOCUMENTS

Figure 1:
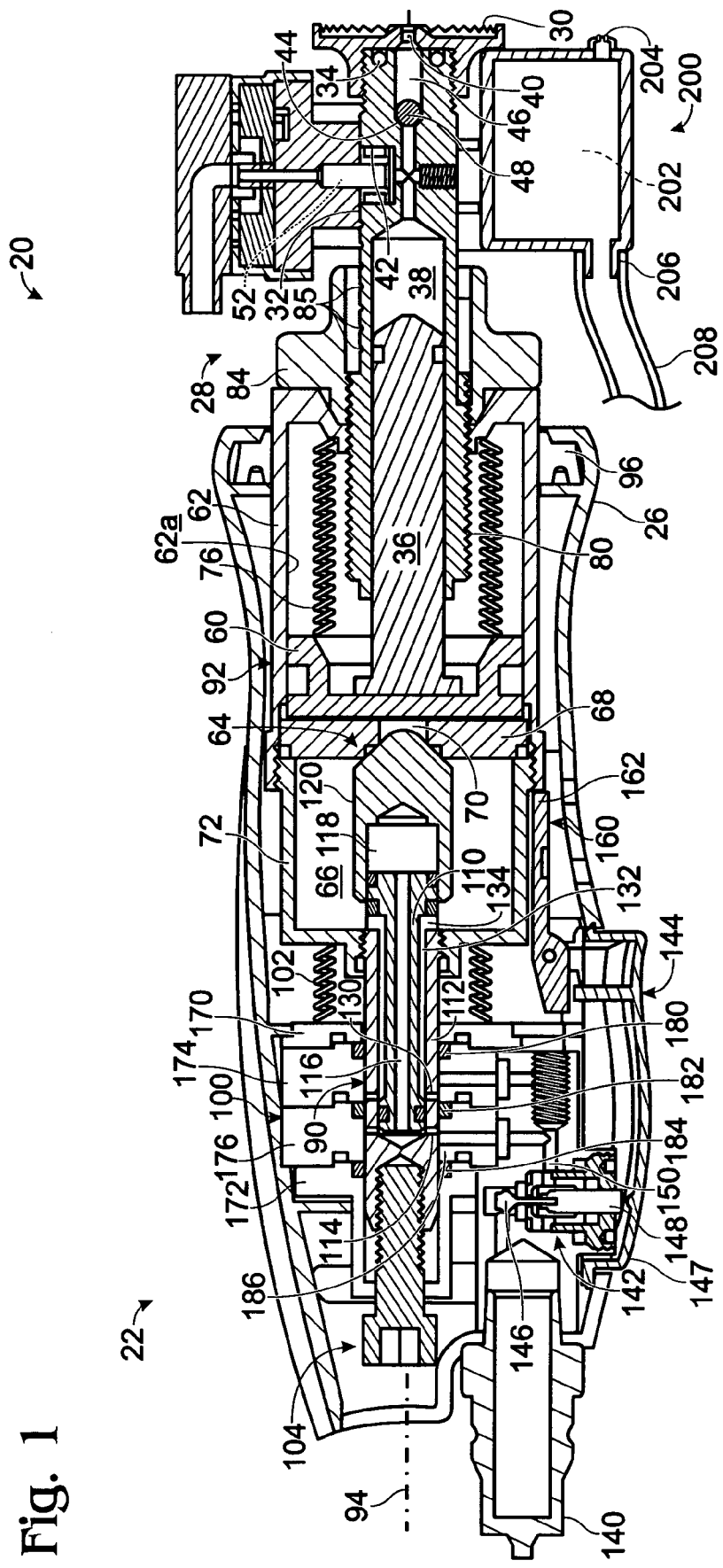

| | | | |
|---|---|---|---|
| 4,680,027 A | 7/1987 | Parsons et al. | |
| 4,717,384 A | 1/1988 | Waldeisen | |
| 4,739,973 A | 4/1988 | Herndon | |
| 4,790,824 A | 12/1988 | Morrow et al. | |
| 4,940,460 A | 7/1990 | Casey, I. et al. | |
| 4,941,880 A | 7/1990 | Burns | |
| 4,966,581 A | 10/1990 | Landau | |
| 5,009,637 A | 4/1991 | Newman et al. | |
| 5,024,656 A | 6/1991 | Gasaway et al. | |
| 5,049,125 A | 9/1991 | Accaries et al. | |
| 5,064,413 A | 11/1991 | McKinnon et al. | |
| 5,312,335 A | 5/1994 | McKinnon et al. | |
| 5,312,577 A | 5/1994 | Peterson et al. | |
| D349,958 S | 8/1994 | Hollis et al. | |
| 5,383,851 A | 1/1995 | McKinnon, Jr. et al. | |
| 5,399,163 A | 3/1995 | Peterson et al. | |
| 5,466,220 A | 11/1995 | Brenneman | |
| 5,503,627 A | 4/1996 | McKinnon et al. | |
| 5,505,697 A | 4/1996 | McKinnon, Jr. et al. | |
| 5,520,639 A | 5/1996 | Peterson et al. | |
| 5,556,031 A | 9/1996 | Cooke et al. | |
| 5,649,912 A | 7/1997 | Peterson | |
| 5,746,714 A | 5/1998 | Salo et al. | |
| 5,782,802 A | 7/1998 | Landau | |
| D399,951 S | 10/1998 | Drach | |
| 5,840,061 A | 11/1998 | Menne et al. | |
| 5,879,327 A | 3/1999 | Moreau DeFarges et al. | |
| 5,891,086 A | 4/1999 | Weston | |
| 5,893,397 A | 4/1999 | Peterson et al. | |
| 5,899,880 A | 5/1999 | Bellhouse | |
| 5,935,111 A * | 8/1999 | Bunyan | 604/191 |
| 5,993,412 A | 11/1999 | Deily et al. | |
| 6,004,287 A | 12/1999 | Loomis et al. | |
| 6,096,002 A | 8/2000 | Landau | |
| 6,132,395 A | 10/2000 | Landau et al. | |
| 6,210,359 B1 | 4/2001 | Patel et al. | |
| 6,224,567 B1 | 5/2001 | Roser | |
| 6,231,540 B1 | 5/2001 | Smedegaard | |
| 6,264,629 B1 | 7/2001 | Landau | |
| 6,264,637 B1 * | 7/2001 | Hogan | 604/191 |
| 6,319,224 B1 | 11/2001 | Stout et al. | |
| 6,383,168 B1 | 5/2002 | Landau et al. | |
| 6,471,669 B2 | 10/2002 | Landau | |
| 6,506,177 B2 | 1/2003 | Landau | |
| 6,544,084 B1 | 4/2003 | Nanami | |
| 6,572,581 B1 | 6/2003 | Landau | |
| 6,585,685 B2 | 7/2003 | Staylor et al. | |
| 6,602,222 B1 | 8/2003 | Roser | |
| 6,607,510 B2 | 8/2003 | Landau | |
| 6,610,042 B2 | 8/2003 | Leon et al. | |
| 6,676,630 B2 * | 1/2004 | Landau et al. | 604/70 |
| 2002/0087117 A1 | 7/2002 | Stout et al. | |
| 2002/0123717 A1 | 9/2002 | Landau | |
| 2002/0123718 A1 | 9/2002 | Landau | |
| 2003/0065286 A1 | 4/2003 | Landau | |
| 2003/0088214 A1 | 5/2003 | Leon et al. | |
| 2003/0093030 A1 | 5/2003 | Landau | |

* cited by examiner

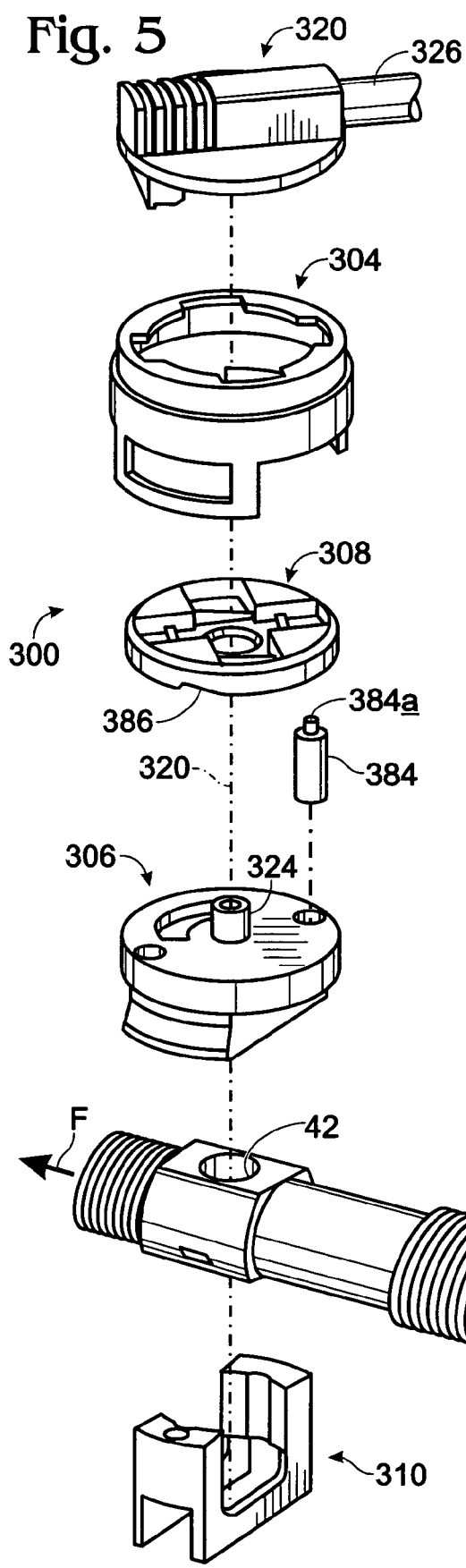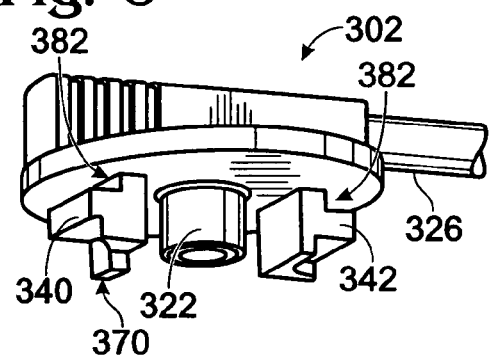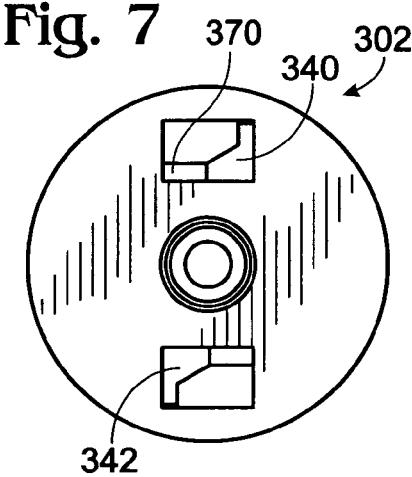

Fig. 8
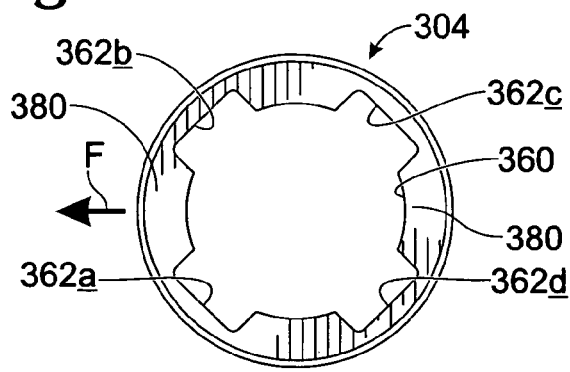
Fig. 9A  Fig. 9B  Fig. 9C
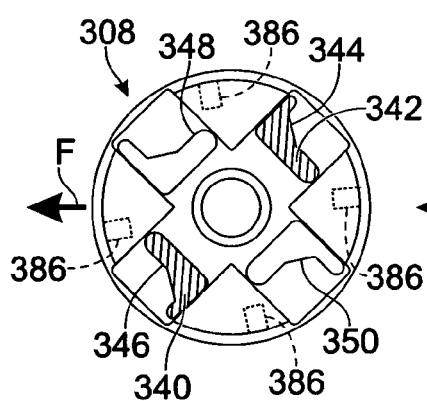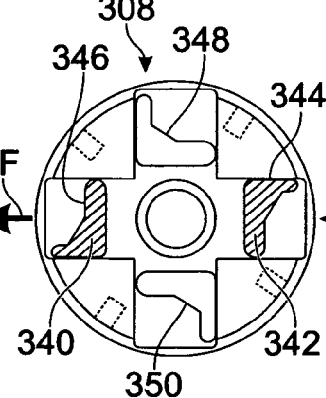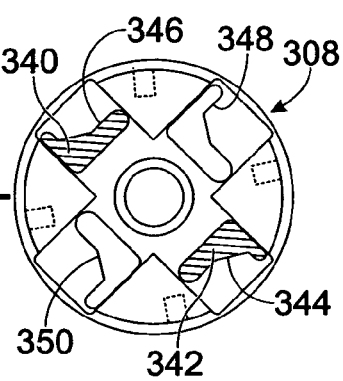
Fig. 10
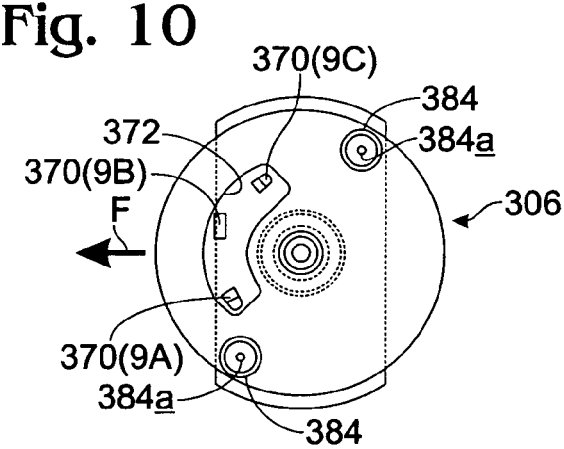

NEEDLE-FREE INJECTION SYSTEM

CROSS REFERENCE TO RELATED APPLICATIONS

This application is a continuation-in-part of U.S. patent application Ser. No. 10/164,920, filed Jun. 4, 2002 now U.S. Pat. No. 6,676,630, the disclosure of which is incorporated in its entirety for all purposes.

BACKGROUND OF THE INVENTION

Needle-free injection systems provide an alternative to standard fluid delivery systems, which typically use a needle adapted to penetrate the outer surface of a target. Typically, needle-free injection systems are designed to eject the fluid from a fluid chamber with sufficient pressure to allow the fluid to penetrate the target to the desired degree. For example, common applications for needle-free injection systems include delivering intradermal, subcutaneous and intramuscular injections into or through a recipient's skin. For each of these applications, the fluid must be ejected from the system with sufficient pressure to allow the fluid to penetrate the tough exterior dermal layers of the recipient's skin.

SUMMARY OF THE INVENTION

The invention provides an improved needle-free injection device. The injection device includes a user-grippable housing and a syringe assembly movably secured to the housing. The syringe assembly is configured to expel injectable fluid out of a nozzle upon application of pressurized gas to the syringe assembly. The injection device also includes a pressurized gas delivery mechanism disposed within the housing and configured to selectively apply pressurized gas to the syringe assembly. The pressurized gas delivery mechanism is at least partly actuated by pressing the nozzle onto an injection site so that the syringe assembly moves relative to the housing.

BRIEF DESCRIPTION OF THE DRAWINGS

FIG. 1 is a sectional side elevation view of a needle-free injection system according to the invention, and depicts the system in a primed position.

FIG. 2 is a sectional side elevation view of the system of FIG. 1 that depicts the system in a charged position.

FIG. 3 is a sectional side elevation view of the system of FIG. 1 that depicts the system after it has been fired.

FIG. 4 is an exploded view of the system of FIG. 1.

FIG. 5 is an isometric exploded view showing structures that may be used to connect a fluid supply to the injection device depicted in FIGS. 1-4.

FIG. 6 is an isometric view of a fluid supply adapter that is also shown in FIG. 5.

FIG. 7 is a bottom view of the fluid supply adapter shown in FIGS. 5 and 6.

FIG. 8 is a top view of a locking ring that is also shown in FIG. 5.

FIGS. 9A, 9B and 9C are top views of a rotatable key member that is also shown in FIG. 5, and show the rotatable key member in three different rotational positions relative to the injection device of FIGS. 1-4.

FIG. 10 is a top view of a base member that is also shown in FIG. 5.

FIG. 11 is a sectional side elevation view of a needle-free injection system according to another embodiment of the invention, and depicts the system in a primed position.

FIG. 12 is a sectional side elevation view of the system of FIG. 11 that depicts the system in a charged position.

FIG. 13 is a sectional side elevation view of the system of FIG. 11 that depicts the system after it has been fired.

FIG. 14 is a sectional top view of the system of FIG. 11 that depicts the system in a primed position.

FIG. 15 is a sectional top view of the system of FIG. 11 that depicts the system after it has been fired.

DETAILED DESCRIPTION OF THE PREFERRED EMBODIMENTS

Construction of the Preferred Embodiments

FIG. 1 depicts a needle-free injection system 20 according to the invention, including an injection device 22. FIG. 1 shows injection device 22 in a first position, which will be referred to as the "primed" or "priming" position. Typically, the device is also placed in the position shown in FIG. 1 for storage and/or shipping. FIG. 2 depicts device 22 in a position which will be referred to as the "primed" or "priming" position; FIG. 3 depicts device 22 in a position which will be referred to as the "fired" or "firing" position. FIG. 4 is an exploded view depicting various components that may be used to construct injection device 22.

As will be explained in more detail below, injection device 22 is configured to inject a dose of a drug or other fluid into a subject animal. This is accomplished by using pressurized gas to expel fluid from the injection device. The pressurized gas may be supplied from a tank, cartridge or other source, and typically is delivered through device 22 and vented via operation of various valve structures. System 20 may include a fluid supply 24 that may be coupled with injection device 22 in order to supply the injection device with fluid, such as drugs, vaccines or other injectable fluids.

As shown, injection device 22 may include an outer housing 26, which typically is adapted to be comfortably held in a user's hand. The depicted housing is formed from injection-molded plastic, though various other materials and fabrication methods may be employed as desired.

Injection device 22 typically includes a fluid expulsion mechanism, such as syringe assembly 28, that is configured to draw in and forcibly expel drugs or other fluids. As shown in the figures, syringe assembly 28 may be disposed at least partially within housing 26 toward a forward end of the housing. Syringe assembly 28 includes a nozzle 30, which is affixed to an end of a fluid cylinder 32 and sealed thereon with an o-ring 34. A plunger 36 is slidably disposed within fluid cylinder 32, thereby defining a variable-volume fluid reservoir 38. When plunger 36 is advanced (i.e., moved to the right in FIGS. 1-3), fluid is expelled out of fluid reservoir 38 through a discharge outlet 40 provided in nozzle 30. Retraction of plunger 36 (i.e., moving the plunger to the left in FIGS. 1-3) draws fluid into fluid reservoir 38 through inlet 42, which typically is coupled with fluid supply 24. It should be appreciated that syringe assembly 28 is presented as an illustrative example only, and that other variable-volume devices may be employed. For example, a squeezable bulb or elastomeric bladder may be used to expel fluid from injection device 22.

In the depicted syringe assembly, outlet 40 and inlet 42 typically are provided with check valves to prevent backflow. Various types of valves may be used, though ball-type check valves have proved useful in the depicted embodiment. Specifically, as indicated in the figures, an outlet check ball 44 is disposed within an outlet check ball chamber 46. Outlet check ball 44 is held against a valve seat 48 as plunger 36 is retracted, to prevent fluid or contaminants from being drawn into fluid reservoir 38 through discharge outlet 40. A spring (not shown) may also be provided to urge the check ball to the left into the closed position. As plunger 36 advances, check ball 44 moves forward, away from engagement with seat 48, allowing fluid to pass around the check ball and out of nozzle 30 through outlet 40. Inlet 42 may also include a similar ball-type check valve 52, including a check ball (not shown) urged upward into a closed position against a valve seat. When plunger 36 retracts, check valve 52 opens, allowing fluid from fluid supply 24 to be drawn through the check ball valve into fluid reservoir 38.

Figure 3:
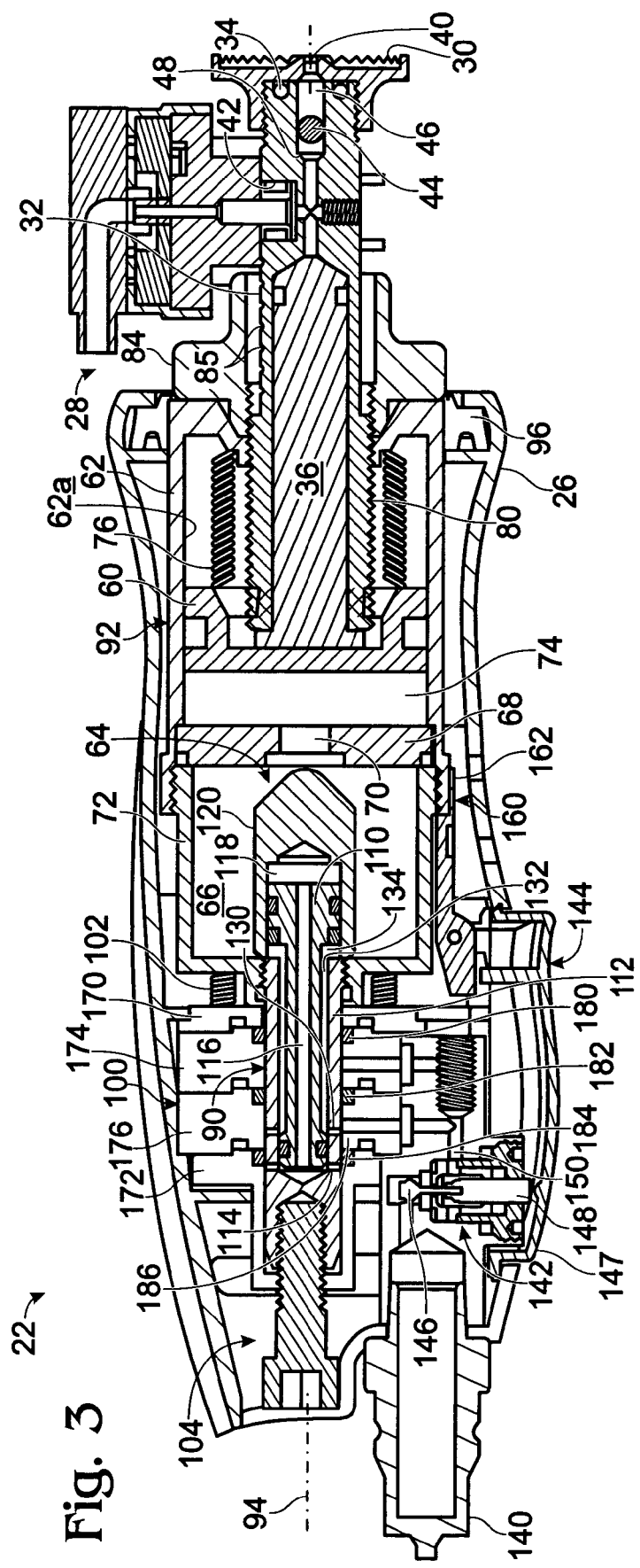
Figure 4:
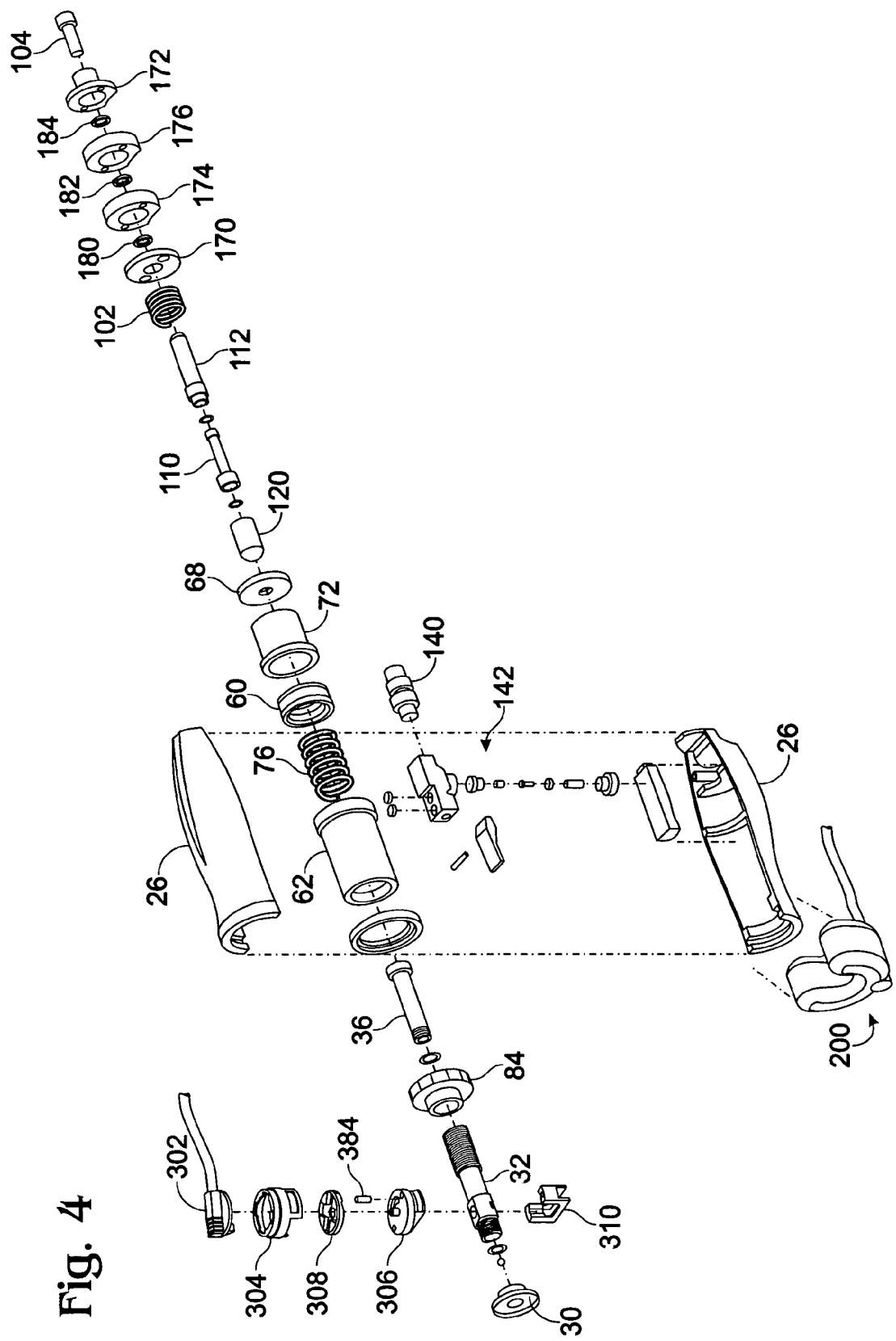

As indicated, a piston 60 may be secured to plunger 36. In the depicted embodiment, piston 60 is slidably disposed within a piston cylinder 62, and creates a substantially sealed interface with an interior wall 62a of the piston cylinder. As will be explained in more detail below, when a poppet valve 64 opens, as shown in FIG. 3, pressurized gas from a gas reservoir 66 is allowed to escape past a gas bulkhead 68 through a bulkhead opening 70. Gas reservoir 66 is contained within a gas cylinder 72, which is fixedly secured relative to bulkhead 68 and piston cylinder 62. Upon the opening of poppet valve 64, the pressurized gas exerts upon operative surface 60a of piston 60, causing piston 60 and plunger 36 to advance forward and expel fluid from syringe assembly 28 through discharge outlet 40. The area between bulkhead 68 and piston 60 created by the advancement of piston 60 will be referred to as piston chamber 74 (FIG. 3). As indicated, a return spring 76 may be provided to urge piston 60 back toward bulkhead 68 upon venting of pressurized gas within piston chamber 74 and gas reservoir 66.

Syringe assembly 28 may be configured with an adjustment capability to allow variation of the maximum amount of fluid that may be drawn into and expelled from fluid reservoir 38. Specifically, as indicated, the outer circumference of fluid cylinder 32 may include threads 80 configured to interface with corresponding threads on piston cylinder 62. Rotation of the fluid cylinder then varies the plunger's permitted range of motion, by adjusting the maximum amount by which plunger 36 may be withdrawn from fluid cylinder 32 before being blocked by bulkhead 68. This adjusts the maximum volume of fluid reservoir 38. A locking nut 84 may also be provided to retain fluid cylinder 32 in place relative to piston cylinder 62 once a desired volume has been selected. Indicia 85 may be provided on the outer surface of the fluid cylinder 32, or in another suitable location, to indicate the selected volume and/or the relative position of fluid cylinder 32 and piston cylinder 62.

As indicated above, piston cylinder 62 typically is fixedly secured to gas bulkhead 68 and gas cylinder 72. Toward the rear half of housing 26, a slidable valve structure 90 is fixedly secured to gas cylinder 72. Piston cylinder 62, gas cylinder 72 and slidable valve structure 90 collectively form a reciprocating structure 92 which moves back and forth relative to housing 26 along axis 94. Syringe assembly 28 is secured to the forward end of reciprocating structure 92, and thus also moves relative to housing 26. The forward end of reciprocating structure 92 is held within an aperture in housing 26, such that at least part of syringe assembly 28 sticks out of the forward end of housing 26. A wiper seal 96 may be provided within the aperture to contact the reciprocating structure (e.g., the outer surface of piston cylinder 62). Toward the rear of reciprocating structure 92, slidable valve structure 90 is slidably supported within a valve body 100 that is fixedly secured within housing 26.

During operation, reciprocating structure 92 is progressively pushed into housing 26 from the position shown in FIG. 1, to the position shown in FIG. 3. Normally, this occurs as a result of pressing nozzle 30 against an injection site while manually gripping housing 26. Spring 102 is compressed as reciprocating structure 92 moves in a rearward direction relative to housing 26. Upon removal of the compressing force, spring 102 urges reciprocating structure 92 back toward the position shown in FIG. 1.

An adjustment bolt 104 or like device may be provided to adjust the degree to which reciprocating structure 92 may be pushed into housing 26. Specifically, as seen at the rear or left end of FIG. 3, the head of bolt 104 abuts the rear portion of the interior of housing 26 to prevent further rearward movement of reciprocating structure 92 relative to housing 26. Rotation of bolt 104 thus adjusts the available range of rearward travel of reciprocating structure 92.

Figure 2:
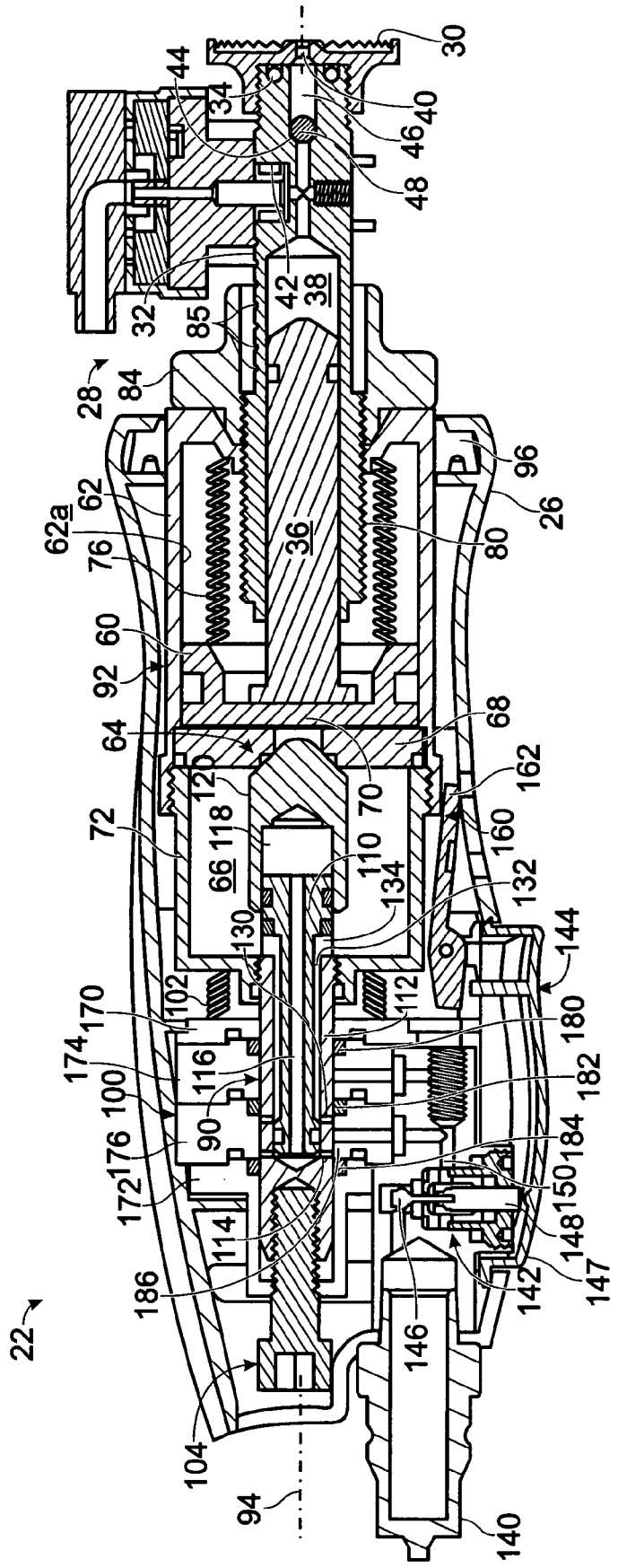

As depicted, slidable valve structure 90 may include an inner valve sleeve 110 and an outer valve sleeve 112. In the depicted exemplary embodiment, outer valve sleeve 112 includes a first set of holes 114 which fluidly communicate with a bore passage 116 defined through the center of inner valve sleeve 110. Bore passage 116 fluidly couples with a poppet reservoir 118 defined in part by poppet 120. In the depicted embodiment, poppet 120 is slidably movable back and forth on the end of slidable valve structure 90. When poppet 120 is in its forward-most position, as shown in FIGS. 1 and 2, poppet 120 seats into a valve seat in bulkhead 68, thus sealing off gas reservoir 66 from piston chamber 74. Fore-and-aft movement of poppet 120 typically is controlled by gas pressure existing in poppet reservoir 118 and gas reservoir 66.

Outer valve sleeve 112 may include another set of holes 130, which fluidly communicate with a cylindrical passage 132. As indicated, passage 132 may be defined between the inner and outer valve sleeves. Cylindrical passage 132 fluidly couples with gas reservoir 66 via holes 134. The external surface of outer valve sleeve 112 may include a single, small groove 135 to provide a gas path between one of holes 130 and one of holes 114. This gas path provides a means of escape for exhaust gas at the conclusion of an injection sequence.

A gas fitting 140 may be provided into housing 26, to enable the injection device to be supplied with compressed air or some other pressurized gas via a gas hose (not shown). The delivery of pressurized gas through the device typically is controlled via a supply valve assembly 142, which is actuated via operation of a trigger 144. As shown, supply valve assembly 142 may include a valve 146 biased into a closed position by a spring (not shown), a supply valve plunger 148 secured to supply valve 146, and a supply conduit 150 through which pressurized gas is provided upon opening of the valve.

Trigger 144 is pivotally movable relative to housing 26 via a hinge 147 provided toward its rear end. Pushing the forward end of trigger 144 inward (or upward as depicted) causes valve plunger 148 to move upward. Upward movement of valve plunger 148 moves supply valve 146 upward into an open position, allowing pressurized gas to pass beyond supply valve 146 and be delivered to other parts of device 22 via a supply conduit 150.

Valve body 100 includes a forward section 170, a rear section 172, and two intermediate sections 174 and 176. A spring 102 extends between and urges against forward section 170 and the rear end of gas cylinder 72. Three U-cup seals 180, 182 and 184 are provided between the pieces of the valve body. The area of intermediate section 176 between seals 182 and 184 provides a supply chamber 186 that is fluidly coupled with supply conduit 150 of supply valve assembly 142. The area of rear section 172 to the rear of seal 184 vents to atmosphere, as does the area of intermediate section 174 forward of seal 180.

Accordingly, it will be appreciated that moving slidable valve structure 90 backward and forward relative to valve body 100 (e.g., by pushing reciprocating structure 92 into housing 26) controls pressurization and venting of the various passages in slidable valve structure 90. Referring to FIG. 3, for example, valve structure 90 is positioned so that holes 114 in outer valve sleeve 112 are aligned slightly to the rear of seal 184, allowing bore passage 116 and poppet reservoir 118 to vent to atmosphere. In FIG. 1, holes 130 are aligned slightly to the front of seal 180, allowing cylindrical passage 132 and gas reservoir 66 to vent to atmosphere. In FIGS. 1-3, holes 114 and/or holes 130 are at times aligned with supply chamber 186, such that the respective passages and reservoirs are equalized in pressure relative to the supply chamber. Accordingly, in such a state of alignment, opening supply valve 146 would pressurize the respective passages/reservoirs.

As seen in FIG. 1, injection device 22 may also include a dye marker 200. Dye marker 200 includes a dye reservoir 202 and a dye outlet 204. A pressure inlet 206 is coupled with a pressure source via a hose 208. Dye marker 200 is configured to apply a metered amount of marking dye to an injection site upon application of air pressure through hose 208. Typically, the pressure source is provided by the residual air pressure in gas reservoir 66 and piston chamber 74 as those areas are vented. Specifically, hose 208 may be coupled to an exhaust port in housing 26 to fluidly couple dye marker 200 with venting passages within injection device 22.

Figure 11:
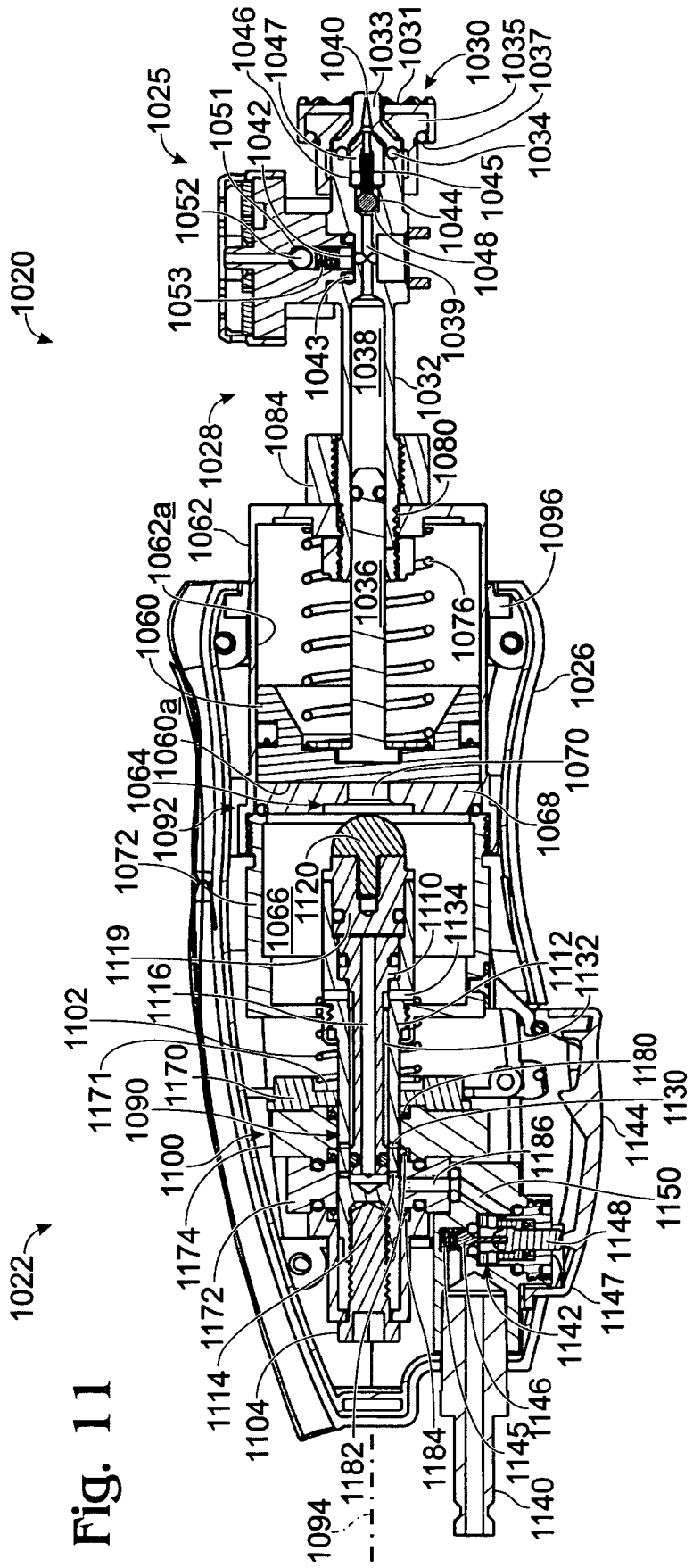
Figure 12:
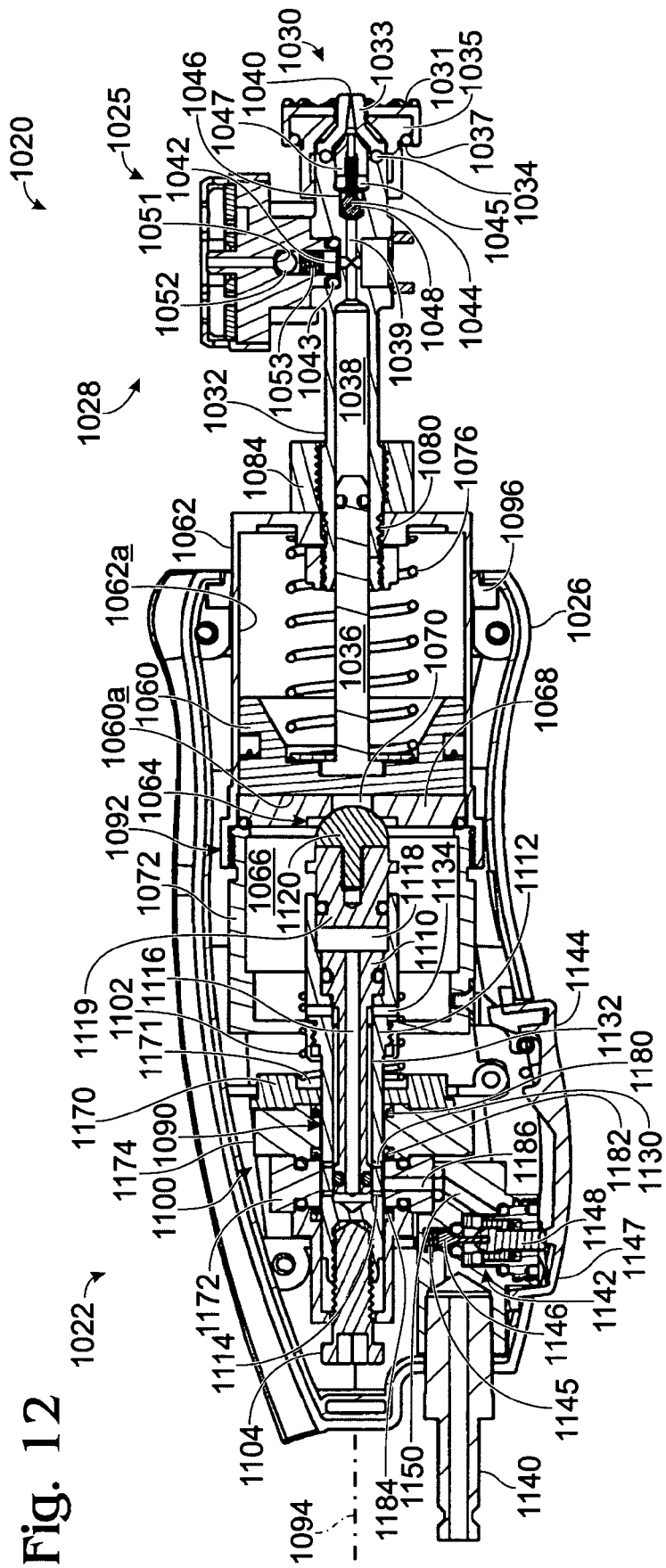
Figure 13:
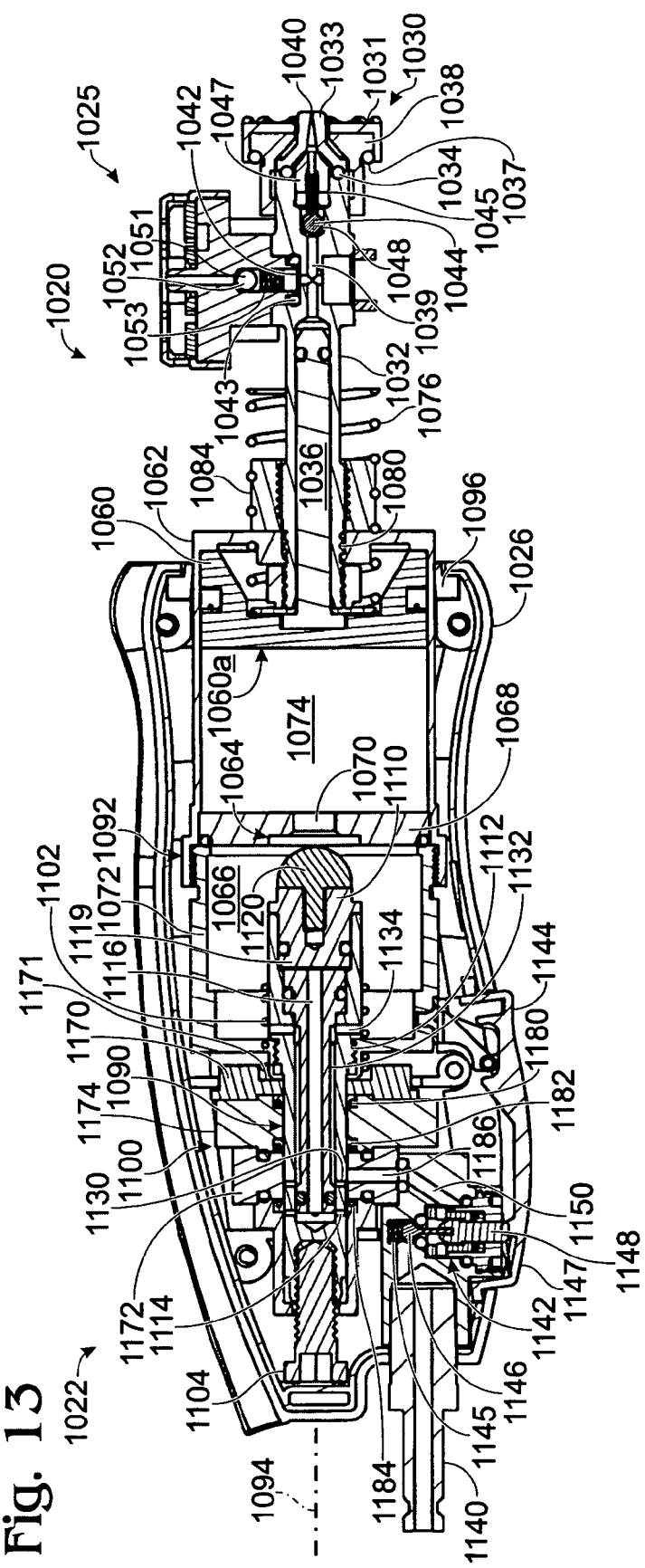
Figure 14:
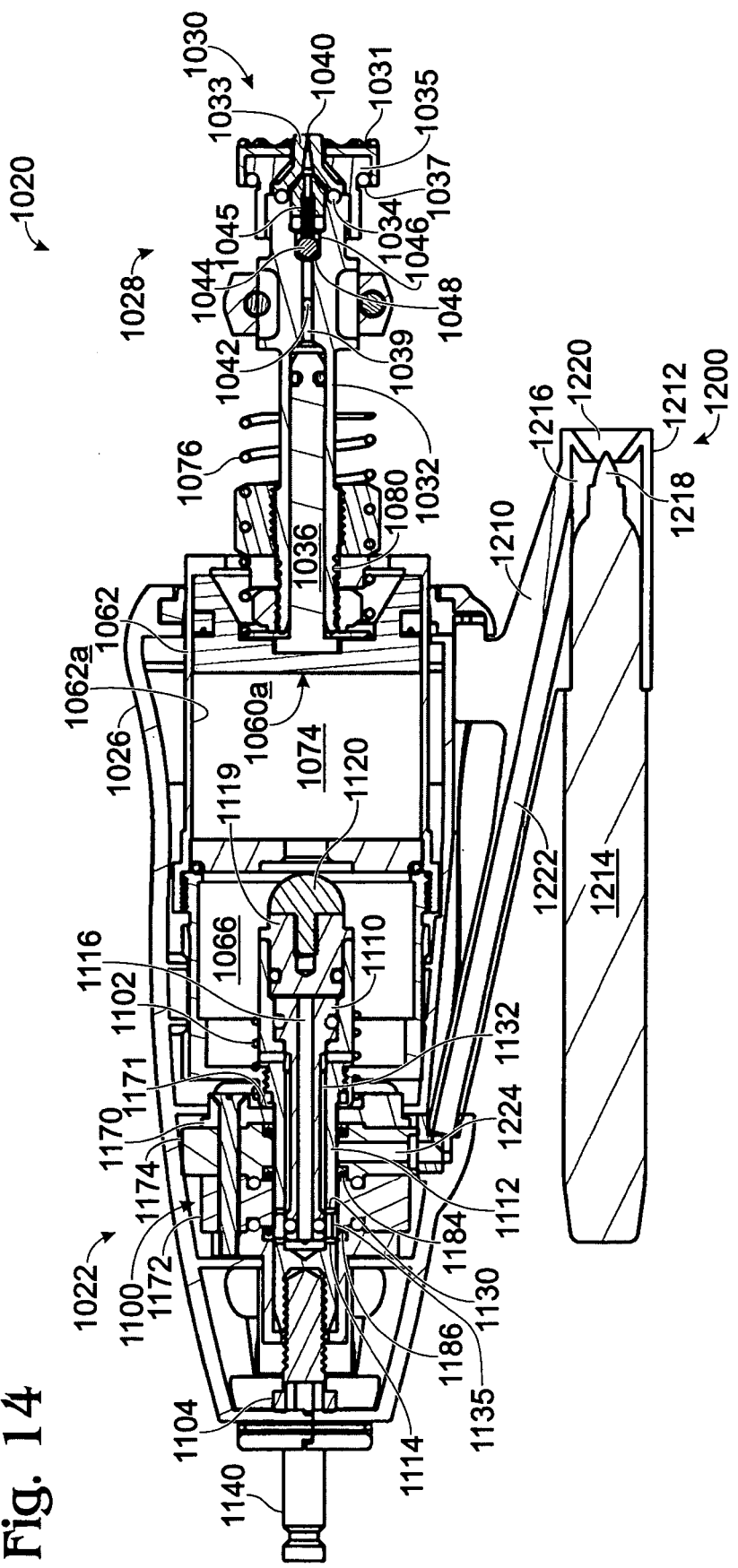
Figure 15:
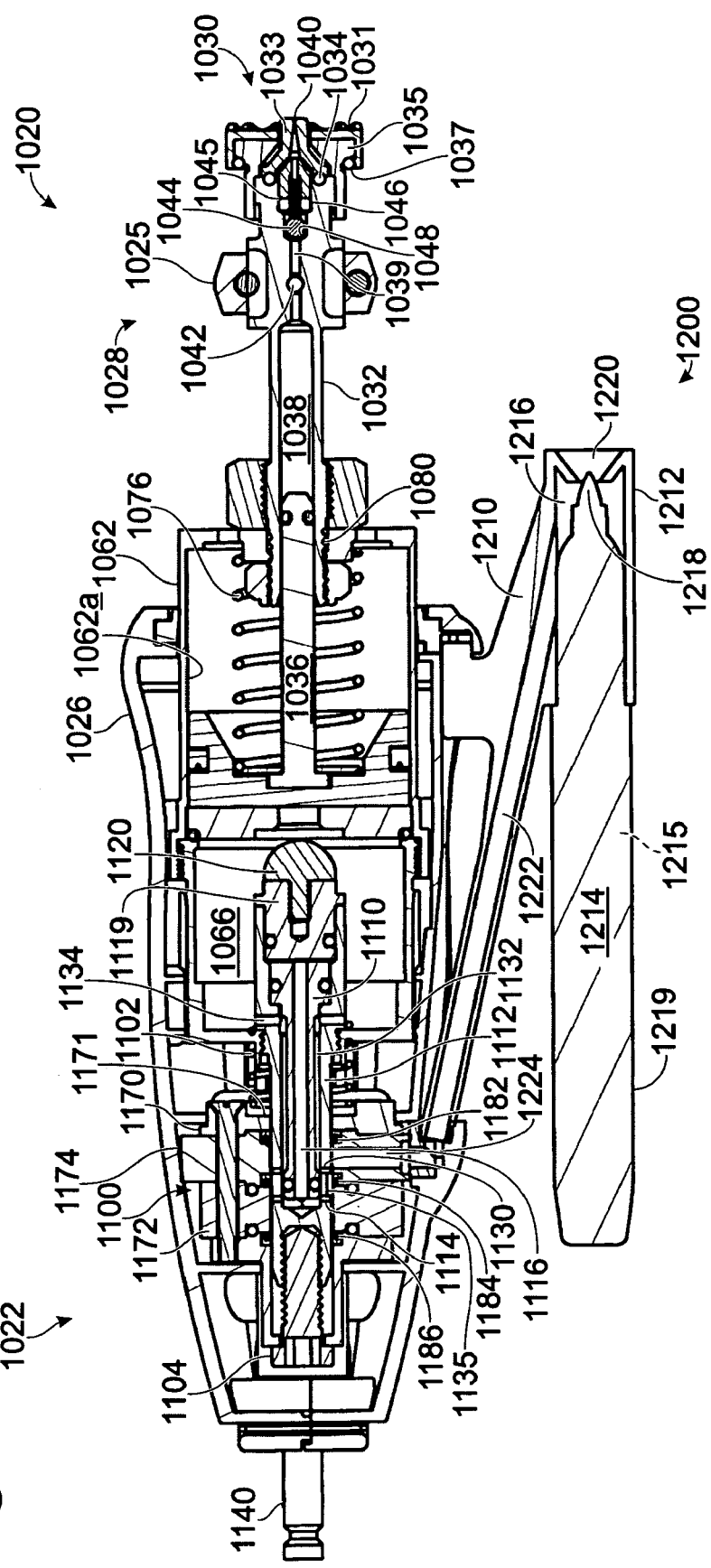

FIGS. 11-15 depict a needle-free injection system 1020 according to another embodiment of the invention. Injection system 1020 includes an injection device 1022. FIG. 11 shows injection device 1022 in a first position. Typically, the device is placed in the position shown in FIG. 11 for storage and/or shipping, and thus, this position may be referred to as the "storage" position. FIG. 12 depicts device 1022 in a position which will be referred to as the "primed," or "priming" position. FIG. 13 depicts device 1022 in a position which will be referred to as the "fired" or "firing" position. FIG. 14 depicts device 1022 in the storage position shown in FIG. 11, but rotated 90 degrees along the horizontal axis to show a top sectional view. FIG. 15 depicts device 1022 in the fired position shown in FIG. 13, but rotated 90 degrees along the horizontal axis to show a top sectional view.

For the sake of clarity those elements of the injection device shown in FIGS. 11-15 that perform the same or a similar function as elements of the injection device described with respect to FIGS. 1-3 are given corresponding reference numbers in the thousands range. For example, where the injection device in FIGS. 1-3 is given the reference number 22, the injection device in FIGS. 11-15 is given the reference number 1022. Moreover, it should be appreciated that any of the elements described with respect to the embodiment shown in FIGS. 1-3 may be incorporated into the device shown in FIGS. 11-15 and vice versa.

As in the embodiment described above with respect to FIGS. 1-3, injection device 1022 is configured-to inject a dose of a drug or other fluid into a subject animal. This is accomplished by using pressurized gas to expel fluid from the injection device. The pressurized gas may be supplied from a tank, cartridge or other source, and typically is delivered through device 1022 and vented via operation of various valve structures. System 1020 may include a fluid supply (not shown) that may be coupled with injection device 1022 in order to supply the injection device with fluid, such as drugs, vaccines or other injectable fluids.

As shown, injection device 1022 may include an outer housing 1026, which typically is adapted to be comfortably held in a user's hand. The depicted housing is formed from injection-molded plastic, though various other materials and fabrication methods may be employed as desired.

Injection device 1022 typically includes a fluid expulsion mechanism, such as syringe assembly 1028, that is configured to draw in and forcibly expel drugs or other fluids. As shown in the figures, syringe assembly 1028 may be disposed at least partially within housing 1026 toward a forward end of the housing. Syringe assembly 1028 includes a disposable nozzle assembly 1030. Detachable nozzle assembly 1030 includes a disposable end cap 1031 and a disposable nozzle 1033. End cap 1031 is detachably connected to a retaining structure 1035, and may be sealed thereon by an o-ring 1037. Nozzle 1033 may be detachably seated into retaining structure 1035, and defines discharge outlet 1040. O-ring 1034 may provide a seal between disposable nozzle 1033 and fluid cylinder 1032. End cap 1031, nozzle 1033, and retaining structure 1035 may be formed out of any suitable material or materials including, for example, plastic or metal. In some embodiments, end cap 1031 and nozzle 1033 may be formed of plastic, while retaining structure 1035 may be formed of metal.

A plunger 1036 is slidably disposed within fluid cylinder 1032, thereby defining a variable-volume fluid reservoir 1038. When plunger 1036 is advanced (i.e., moved to the right in FIGS. 11-14), fluid is expelled out of fluid reservoir 1038 via fluid path 1039 and through a discharge outlet 1040 provided in nozzle 1030. Retraction of plunger 1036 (i.e., moving the plunger to the left in FIGS. 11-15) draws fluid into fluid reservoir 1038 through inlet 1042, which typically is coupled with a fluid supply via connecting assembly 1025. The connection between inlet 1042 and fluid path 1039 may be sealed by an o-ring 1043. It should be appreciated that syringe assembly 1028 is presented as an illustrative example only, and that other variable-volume devices may be employed. For example, a squeezable bulb or elastomeric bladder may be used to expel fluid from injection device 1022.

In the depicted syringe assembly, outlet 1040 and inlet 1042 typically are provided with check valves to prevent backflow. Various types of valves may be used, including ball-type check valves. Specifically, as indicated in the figures, an outlet check ball 1044 is disposed within an outlet check ball chamber 1046. Outlet check ball 1044 is held against a valve seat 1048 as plunger 1036 is retracted, to prevent fluid or contaminants from being drawn into fluid reservoir 1038 through discharge outlet 1040. A spring 1045 may also be provided to urge the check ball towards valve seat 1048 and into the closed position. Spring 1045 may be retained in place by a retaining structure 1047. Retaining structure 1047 may, for example, be formed of plastic or any other suitable material. As plunger 1036 advances, check ball 1044 moves forward, away from engagement with seat 1048, allowing fluid to pass around the check ball and out of nozzle 1030 through outlet 1040. Inlet 1042 may also include a similar ball-type check valve including a check ball 1052 urged upward into a closed position against a valve seat 1051. Again, a spring 1053 may be provided to urge check ball 1052 into valve seat 1051 and into the closed position. When plunger 1036 retracts, check valve 1052 opens, allowing fluid from fluid supply 1024 to be drawn through the check ball valve into fluid reservoir 1038.

As indicated, a piston 1060 may be secured to plunger 1036. In the depicted embodiment, piston 1060 is slidably disposed within a piston cylinder 1062, and creates a substantially sealed interface with an interior wall 1062a of the piston cylinder. As will be explained in more detail below, when a poppet valve 1064 opens, as shown in FIG. 13, pressurized gas from a gas reservoir 1066 is allowed to escape past a gas bulkhead 1068 through a bulkhead opening 1070. Gas reservoir 1066 is contained within a gas cylinder 1072, which is fixedly secured relative to bulkhead 1068 and piston cylinder 1062. Upon the opening of poppet valve 1064, the pressurized gas exerts upon operative surface 1060a of piston 1060, causing piston 1060 and plunger 1036 to advance forward and expel fluid from syringe assembly 1028 through discharge outlet 1040. The area between bulkhead 1068 and piston 1060 created by the advancement of piston 1060 will be referred to as piston chamber 1074 (FIG. 13). As indicated, a return spring 1076 may be provided to urge piston 1060 back toward bulkhead 1068 upon venting of pressurized gas within piston chamber 1074 and gas reservoir 1066.

Syringe assembly 1028 may be configured with an adjustment capability to allow variation of the maximum amount of fluid that may be drawn into and expelled from fluid reservoir 1038. Specifically, as indicated, the outer circumference of fluid cylinder 1032 may include threads 1080 configured to interface with corresponding threads on piston cylinder 1062. Rotation of the fluid cylinder then varies the plunger's permitted range of motion, by adjusting the maximum amount by which plunger 1036 may be withdrawn from fluid cylinder 1032 before being blocked by bulkhead 1068. This adjusts the maximum volume of fluid reservoir 1038. A locking nut 1084 may also be provided to retain fluid cylinder 1032 in place relative to piston cylinder 1062 once a desired volume has been selected. While not shown, as with the embodiment described with respect to FIGS. 1-3, indicia may be provided on the outer surface of the fluid cylinder 1032, or in another suitable location, to indicate the selected volume and/or the relative position of fluid cylinder 1032 and piston cylinder 1062.

As indicated above, piston cylinder 1062 typically is fixedly secured to gas bulkhead 1068 and gas cylinder 1072. Toward the rear half of housing 1026, a slidable valve structure 1090 is fixedly secured to gas cylinder 1072. Piston cylinder 1062, gas cylinder 1072 and slidable valve structure 1090 collectively form a reciprocating structure 1092 which moves back and forth relative to housing 1026 along axis 1094. Syringe assembly 1028 is secured to the forward end of reciprocating structure 1092, and thus also moves relative to housing 1026. The forward end of reciprocating structure 1092 is held within an aperture in housing 1026, such that at least part of syringe assembly 1028 sticks out of the forward end of housing 1026. A wiper seal 1096 may be provided within the aperture to contact the reciprocating structure (e.g., the outer surface of piston cylinder 1062). Toward the rear of reciprocating structure 1092, slidable valve structure 1090 is slidably supported within a valve body 1100 that is fixedly secured within housing 1026.

During operation, reciprocating structure 1092 is progressively pushed into housing 1026 from the position shown in FIG. 11, to the position shown in FIG. 13. Normally, this occurs as a result of pressing nozzle 1030 against an injection site while manually gripping housing 1026. Spring 1102 is compressed as reciprocating structure 1092 moves in a rearward direction relative to housing 1026. Upon removal of the compressing force, spring 1102 urges reciprocating structure 1092 back toward the position shown in FIG. 11.

An adjustment bolt 1104 or like device may be provided to adjust the degree to which reciprocating structure 1092 may be pushed into housing 1026. Specifically, as seen at the rear or left end of FIG. 13, the head of bolt 1104 abuts the rear portion of the interior of housing 1026 to prevent further rearward movement of reciprocating structure 1092 relative to housing 1026. Rotation of bolt 1104 thus adjusts the available range of rearward travel of reciprocating structure 1092.

As depicted, slidable valve structure 1090 may include an inner valve sleeve 1110 and an outer valve sleeve 1112. In the depicted exemplary embodiment, outer valve sleeve 1112 includes a first set of holes 1114 which fluidly communicate with a bore passage 1116 defined through the center of inner valve sleeve 1110. Bore passage 1116 fluidly couples with a poppet reservoir 1118 defined in part by poppet seat 1119. Poppet seat 1119 is adapted to retain a poppet 1120. In the depicted embodiment, poppet seat 1119 is slidably movable back and forth on the end of slidable valve structure 1090. When poppet seat 1119 is in its forward-most position, as shown in FIG. 12, poppet 1120 seats into a valve seat in bulkhead 1068, thus sealing off gas reservoir 1066 from piston chamber 1074. Fore-and-aft movement of poppet seat 1119 typically is controlled by gas pressure existing in poppet reservoir 1118 and gas reservoir 1066.

Outer valve sleeve 1112 may include another set of holes 1130, which fluidly communicate with a cylindrical passage 1132. As indicated, passage 1132 may be defined between the inner and outer valve sleeves. Cylindrical passage 1132 fluidly couples with gas reservoir 1066 via holes 1134. The external surface of the outer valve sleeve 1112 may include a single, small groove, 1135 (shown in FIGS. 14 and 15) to provide a gas path between one of holes 130 and one of holes 114. This gas path provides a means of escape for exhaust gas at the conclusion of an injection sequence.

A gas fitting 1140 may be provided into housing 1026, to enable the injection device to be supplied with compressed air or some other pressurized gas via a gas hose (not shown). The delivery of pressurized gas through the device typically is controlled via a supply valve assembly 1142, which is actuated via operation of a trigger 1144. As shown, supply valve assembly 1142 may include a valve 1146 biased into a closed position by a spring 1145, a supply valve plunger 1148 secured to supply valve 1146, and a supply conduit 1150 through which pressurized gas is provided upon opening of the valve.

Trigger 1144 is pivotally movable relative to housing 1026 via a hinge 1147 provided toward its rear end. Pushing the forward end of trigger 1144 inward (or upward as depicted) causes valve plunger 1148 to move upward. Upward movement of valve plunger 1148 moves supply valve 1146 upward into an open position, allowing pressurized gas to pass beyond supply valve 1146 and be delivered to other parts of device 1022 via a supply conduit 1150.

Valve body 1100 includes a forward section 1170, a rear section 1172, and an intermediate section 1174. A spring 1102 extends between and urges against a recessed region 1171 of forward section 1170 and the rear end of gas cylinder 1072. Three U-cup seals 1180, 1182 and 1184 are provided between the pieces of the valve body. The area of rear section 1172 between seals 1182 and 1184 provides a supply chamber 1186 that is fluidly coupled with supply conduit 1150 of supply valve assembly 1142.

Accordingly, it will be appreciated that moving slidable valve structure 1090 backward and forward relative to valve body 1100 (e.g., by pushing reciprocating structure 1092 into housing 1026) controls pressurization and venting of the various passages in slidable valve structure 1090. Referring to FIG. 13, for example, valve structure 1090 is positioned so that holes 1114 in outer valve sleeve 1112 are aligned slightly to the rear of seal 1184, allowing bore passage 1116 and poppet reservoir 1118 to vent to atmosphere. In FIG. 11, holes 1130 are aligned slightly to the front of seal 1182, allowing cylindrical passage 1132 and gas reservoir 1066 to vent to atmosphere. In FIGS. 11-13, holes 1114 and/or holes 1130 are at times aligned with supply chamber 1186, such that the respective passages and reservoirs are equalized in pressure relative to the supply chamber. Accordingly, in such a state of alignment, opening supply valve 1146 would pressurize the respective passages/reservoirs.

As seen in FIGS. 14 and 15, injection device 1022 may also include a marking assembly 1200. Marking assembly 1200 is connected to outer housing 1026 of device 1022 by supporting structure 1210. As shown, supporting structure 1210 may terminate in a housing 1212, which is adapted to receive and secure a fluid reservoir 1214. Typically, fluid reservoir 1214 includes a fluid chamber 1215 in fluid communication with a nib 1218, which extends out of the fluid chamber. Nib 1218 typically acts as a wick, drawing fluid out of reservoir 1214. Typically, reservoir 1214 holds ink or some other fluid capable of leaving a detectable mark on the surface (i.e., skin, hide, or hair) of an injection recipient. In the depicted embodiment, fluid reservoir 1214 may take the form of a writing instrument, or marker 1219. Suitable markers include the Sharpie® writing instruments sold by Sanford Corp. (Bellwood, Ill.).

As shown, housing 1212 defines a chamber 1216 near nib 1218 of marker 1202. Chamber 1216 includes an outlet 1220, surrounding nib 1218. Outlet 1220 may, for example, be conical in shape, extending from nib 1218 outwards, as shown, thereby creating a shaped venture channel. Air passage 1222 extends from chamber 1216 through supporting structure 1210 and into device 1022, where it communicates with supply conduit 1224. Supply conduit 1224 is adapted to communicate with holes 1130 in slidable valve structure 1090 when the slidable valve structure is moved from the fired position (shown in FIG. 14) to the storage position (shown in FIG. 15). Thus, after an injection, at least a portion of the exhaust gas in gas reservoir 1066 and piston chamber 1074 may be vented into chamber 1216, such that the airflow through chamber 1216 is directed past nib 1218, drawing fluid from nib 1218 out of outlet 1220 and onto the surface of the injection recipient.

Operation of the Depicted Injection Devices

The operation of injection device 22 will now be described with reference to FIGS. 1-3. It should be appreciated that, unless otherwise indicated, injection device 1022 will operate in a substantially similar manner. Injection device 22 is prepared for initial use by coupling a hose (not shown) from a compressed air tank or other supply of pressurized gas to fitting 140. Injection device 22 is then fired one or more times, in the manner to be described below, in order to expel air from fluid reservoir 38 and draw a full metered dose of injectable fluid into the fluid reservoir. Operation of the injection device will be described assuming the device is initially in the position shown in FIG. 1.

First, the operator grips outer housing 26, and presses trigger 144 inward, opening supply valve 146, which causes pressurized gas to flow through supply conduit 150 into supply chamber 186. In the storage position shown in FIG. 1, holes 114 are aligned with supply chamber 186. Bore passage 116 is thus pressurized by the opening of supply valve 146, which causes poppet 120 to move forward and close the poppet valve, sealing off bulkhead 68 between gas reservoir 66 and piston chamber 74.

Trigger 144 is depressed further, causing reciprocating structure 92 to be pushed somewhat into housing 26, moving device 22 from the storage position shown in FIG. 1 to the primed position shown in FIG. 2. In FIG. 2, holes 114 are still aligned with supply chamber 186, but the slidable valve assembly has moved far enough rearward so that holes 130 are now also aligned with supply chamber 186. Thus, gas reservoir 66 is pressurized (charged) via holes 130 and cylindrical passage 132. Poppet reservoir 118 remains pressurized in FIG. 2, such that poppet valve 64 is held closed and no gas escapes into piston chamber 74. Plunger 36 thus remains in its fully withdrawn position. Though FIG. 2 shows trigger 144 un-depressed, it should be appreciated that the trigger is held depressed long enough to allow air delivered through supply valve 146 to charge gas reservoir 66.

As the operator continues to push housing 26 against the injection site, reciprocating structure 92 is pushed further into the housing. At some point, slidable valve structure 90 slides far enough rearward so that holes 114 pass beyond U-cup seal 184, as seen in FIG. 3, which shows the injection device in the firing position. When holes 114 pass beyond seal 184, poppet reservoir 118 is allowed to vent to atmosphere through bore passage 116. At this point, there is a high pressure differential between gas reservoir 66 and atmosphere (e.g., 800 p.s.i. or greater), which causes poppet 120 to move rapidly away from bulkhead 68 and into its rearmost position.

This opens poppet valve 64, which causes the pressurized gas that was contained within gas reservoir 66 to act upon operative surface 60a of piston 60, causing injectable fluid to be rapidly expelled from fluid reservoir 38 through nozzle 30. The expulsion of the injectable fluid forces outlet check ball 44 forward, and the injectable fluid passes through check ball chamber 46 around the outside of the check ball. Check ball 44 and check ball chamber 46 should be sized so that there is sufficient clearance around check ball 44 when it is in its forward position toward nozzle 30. In the depicted embodiment, there is approximately 0.007 inches of clearance around all sides of check ball 44 when in its advanced position. The expulsion of injectable fluid out of fluid reservoir 38 also aids in maintaining inlet check valve 52 closed, to prevent injectable fluid from flowing back into the fluid supply.

As seen in FIG. 3, poppet 120 may be sized so that it covers holes 134 when in its rearmost position. This closes off channel 132 to prevent unnecessary waste of pressurized gas, by preventing further delivery of gas into gas reservoir 66.

FIG. 3 shows piston 60 in its fully advanced position, and reciprocating structure 92 in its rearmost position relative to housing 26. At this point, gas reservoir 66 and piston chamber 74 have not yet vented, and those areas remain at a substantial pressure differential above atmosphere. Piston 60 thus remains advanced. As housing 26 is withdrawn from the injection site, spring 102 urges reciprocating structure 92 forward relative to housing 26. This in turn causes slidable valve structure 90 to move relative to valve body 100. Eventually, gag reservoir 66 and piston chamber 74 are vented when holes 130 and groove 135 of valve structure 90 pass forward beyond U-cup seal 180. As the pressure is released, spring 76 urges against piston 60, causing it to return from its advanced position to its retracted position against bulkhead 68, as seen in FIGS. 1 and 2. In the embodiment shown in FIGS. 1-3, the exhaust gas may be used to actuate dye marker 200, by fluidly coupling the venting chamber and dye marker with hose 208. In the embodiment shown in FIGS. 11-15, the exhaust gas may be directed past nib 1218, drawing marking fluid from nib 1218, out of outlet 1220, and onto the surface of the injection recipient.

As piston 60 retracts, plunger 36 is retracted from its advanced position within fluid reservoir 38. The retreat of plunger 36 opens inlet check valve 52 and draws a new dose of fluid into fluid reservoir 38. The outlet check valve remains closed, due to its spring and the vacuum pressure created by the retraction of plunger 36. Eventually, the device returns to the position shown in FIG. 1 and is ready to deliver another injection of fluid in the manner just described.

Construction and Operation of Fluid Supply Fittings

It should be appreciated that many different types of fluids may be used in connection with the embodiments described above. For example, the device may be used with more than one type of injectable drug. In medical and veterinary applications, it will often be critical that the device is cleaned between uses with different types of injectable fluid. Alternatively, even where one type of injectable fluid is repeatedly used, it will often be desirable and/or necessary to periodically clean the injection device. For example, when a multi-use device is repeatedly used with the same injectable fluid, the fluid can crystallize in the channels and valves that form the fluid path, clogging and obstructing the flow. Accordingly, it will often be desirable to clean the device every time that a container of injectable fluid is exhausted, prior to coupling a new container to the device. Typically, a cleaning fluid is used to clean the device.

FIG. 5 depicts a fitting assembly 300 for connecting a fluid supply to syringe assembly 28. As will be explained in detail below, fitting assembly 300 may be configured to ensure that cleaning fluid is used between different types of injectable fluid. This is accomplished through use of two different types of adapter structures: one for injectable fluids, and a second for cleaning fluid. After an injectable fluid adapter is disconnected, another injectable fluid adapter cannot be coupled to the fitting assembly until a cleaning fluid adapter has been used.

Referring more particularly to FIG. 5, exemplary fitting assembly 300 is shown in an exploded view. FIGS. 6-10 depict different components of the fitting assembly and an adapter 302 that may be used to connect a fluid supply to the fitting assembly. FIGS. 6-10 also illustrate an exemplary method of operation. Fitting assembly 300 includes a locking member 304, a base 306 and a rotatable key member 308. These components are fitted together and secured to fluid cylinder 32 so that they are centered over inlet 42. A collar 310 may wrap around fluid cylinder 32 and connect to the underside of base 306. Collar 310, base 306 and locking member 304 are fixed relative to fluid cylinder 32, while rotatable key member 308 is rotatable about axis 320.

FIG. 5 also partially depicts a fluid supply, including adapter 302, which is configured to couple with fitting assembly 300. When adapter 302 is coupled to fitting assembly 300, fluid may be drawn from the fluid supply into fluid cylinder 32. Referring specifically to FIG. 6 (an isometric view of adapter 302), the adapter includes a cylindrical fitting 322 that fits over a corresponding fitting 324 provided on base 306. Fluid is drawn through a hose 326, through passages defined through fittings 322 and 324, and through inlet 42 into fluid cylinder 32.

The underside of adapter 302 includes a key structure having two protruding legs 340 and 342. Legs 340 and 342 have a generally L-shaped cross section, and are adapted to be received in corresponding L-shaped slots provided through rotatable key member 308. Specifically, as seen in FIGS. 9A, 9B and 9C, rotatable key member 308 includes two opposed pairs of slots: (1) slots 344 and 346, and (2) slots 348 and 350. The spacing between slots 344 and 346 differs from the spacing between slots 348 and 350. Depicted adapter 302 is sized so that its legs fit only into one of the pairs of slots. A second type of adapter is used for the other pair of slots.

Referring now primarily to FIGS. 8-10, the operation of the fitting assembly and adapters will be described. In each of FIGS. 8-10, a leftward pointing arrow (labeled "F") indicates the orientation of the depicted structure relative to the front of injection device 22 (FIG. 5 also shows F near fluid cylinder 32, indicating the front of the injection device). Adapter 302 is first inserted through aperture 360 provided through locking member 304. Aperture 360 is formed to have a number of widened cutout areas 362 (individually designated with letters a, b, c and d) located symmetrically around the aperture. The legs of adapter 302 are sized so that they must be aligned with an opposed pair of cutout areas 362 in order to fit through aperture 360.

Specifically, leg 340 is aligned with cutout area 362*a* and leg 342 is aligned with cutout area 362*c*. The legs are then inserted through aperture 360 so that the legs are received within the corresponding slots on rotatable key member 308. In particular, leg 340 is received within slot 346 and leg 342 is received within slot 344, as seen in FIGS. 9A, 9B and 9C. Also, tab 370, which extends from the bottom of leg 340 (FIGS. 6 and 7), extends into and is received within an arcuate slot 372 provided in base 306 (FIG. 10).

Once adapter 302 is fitted onto fitting assembly as just described, the adapter may be rotated clockwise up to ninety degrees from its initial inserted position. The corresponding rotational position of rotatable key member 308 is progressively shown in FIGS. 9A, 9B and 9C. FIG. 9A corresponds to the initial position of adapter 302 just after it is mounted onto fitting assembly 300. The corresponding position of tab 372 within slot 370 is designated 370(9A) in FIG. 10.

FIG. 9B shows the orientation of adapter 302 and rotatable key member 308 after they have been rotated 45 degrees clockwise from the orientation shown in FIG. 9A. In this position, the adapter is locked into place and the fluid supply is ready to deliver fluid to fluid cylinder 32 (FIGS. 1-5). The corresponding position of tab 370 within slot 372 is designated as 370(9B) in FIG. 10. Adapter 302 is retained in place by edge portions 380 of locking member aperture 360. Specifically, edge portions 380 are held within slots 382, which are defined in part by the legs of adapter 302, in order to prevent the adapter from pulling upward off of fitting assembly 300.

After use, adapter 302 is rotated another 45 degrees in a clockwise direction, so that rotatable key member 308 and adapter 302 are rotated into the position shown in FIG. 9C. The corresponding position of tab 370 within slot 372 is designated as 370(9C) in FIG. 10. In this position, legs 340 and 342 align with cutouts 362*b* and 362*d*, allowing the adapter to be pulled through locking member 304 and decoupled from fitting assembly 300.

In FIG. 9C, rotatable key member has been rotated 90 degrees from the position shown in FIG. 9A, such that slots 350 and 348 are aligned with cutout areas 362a and 362c. As discussed above, adapter 302 does not match with slots 350 and 348, because of the different spacing between the slots. Therefore, if the user attempts to insert the adapter through locking member 304 by aligning adapter legs 340 and 342 with cutout areas 362a and 362c, rotatable key member 308 will obstruct the adapter and prevent it from being fully mounted on fitting assembly 300. Instead, a second type of adapter must be used, having legs that are configured to be received within slots 350 and 348.

Fitting assembly 300 typically is configured to constrain rotation of rotatable key member 308. As seen in FIGS. 5 and 10, base 306 may include depressible structures 384, which each have a nub 384a that is resiliently urged toward rotatable key member 308 (upward in FIG. 5). Depressible structures 384 may take the form of a ball joints, leaf springs, spring plungers or other suitable structures. The facing surface of rotatable key member 308 includes a plurality of detents 386 in which nubs 384a may be received, depending on the rotational position of rotatable key member 308. Detents 386 have an asymmetrical shape, in order to produce a ratchet-type effect, in which a given detent can only move in one direction (e.g., clockwise rotation of rotatable key member 308, as in the depicted embodiment) past a nub.

Typically, depressible structures 384 also extend into the slots in rotatable key member 308, to lock rotatable key member in various different rotational positions relative to base 306. For example, when rotatable key member 308 is in the position shown in FIG. 9A, nubs 384a extend upward into slots 344 and 346. Specifically, as shown in FIG. 9A, slots 344 and 346 each have an outer-most rounded leg portion adjacent the edge of rotatable key member 308. When rotatable key member 308 is in the position shown in FIG. 9A, the depressible structures extend upward into these rounded leg portions to lock the rotatable key member in place and prevent it from rotating. Rotatable key member 308 is unlocked by inserting an appropriately sized adapter, as explained below.

The interaction described above between depressible structures 384 and rotatable key member 308 may be used to require alternating use of different types of adapters with fitting assembly 300. For purposes of illustration, a fluid supply adapter with legs sized to fit into slots 344 and 346 (e.g., adapter 302) will be referred to as a "Type A" adapter. An adapter with legs sized to fit into slots 348 and 350 will be referred to as a "Type B" adapter (not shown).

Beginning with FIG. 9A, prior to insertion of the Type A adapter (i.e., adapter 302), depressible structures 384 extend into slots 344 and 346 to rotationally lock rotatable key member 308 in place. To unlock rotatable key member 308, the Type A adapter is inserted, as shown in FIG. 9A, so that the adapter legs depress nubs 384a and force them out of their inserted positions within slots 344 and 346.

With rotatable key member thus unlocked, Type A adapter 302 and rotatable key member 308 are free to rotate 45 degrees clockwise into the operational position shown in FIG. 9B. In this position, depressible structures 384 are received within an opposed pair of detents 386. This prevents counter-clockwise rotation of rotatable key member 308 back into the position shown in FIG. 9A, requiring the user to rotate the device clockwise into the position shown in FIG. 9C in order to remove type A adapter 302.

Accordingly, when the operator desires to remove Type A adapter 302 (for example, after emptying a container of vaccine), the adapter and rotatable key member 308 are rotated into the position shown in FIG. 9C. In this position, depressible structures lock into slots 348 and 350, to prevent any further rotation of rotatable key member 308. At this point, a Type B adapter must be used to unlock rotatable key member 308, because the spacing between slots 348 and 350 differs from the spacing between slots 344 and 346.

This requires the user to alternate between Type A and Type B adapters. After using and removing a Type A adapter (e.g., with a particular vaccine), another Type A adapter cannot be used until a Type B adapter is connected to and removed from fitting assembly. This can be advantageously employed to require use of a cleaning fluid between different types of injectable fluids, or before replacing a spent fluid supply, such as a vaccine container, with another supply of the same type of injectable fluid. Also, a storage cap may be provided in the form of a Type A adapter, requiring the operator to clean the device (e.g., with a Type B adapter and cleaning fluid) both before and after using the storage cap.

While the present invention has been particularly shown and described with reference to the foregoing preferred embodiments, those skilled in the art will understand that many variations may be made therein without departing from the spirit and scope of the invention as defined in the following claims. The description of the invention should be understood to include all novel and non-obvious combinations of elements described herein, and claims may be presented in this or a later application to any novel and non-obvious combination of these elements. Where the claims recite "a" or "a first" element or the equivalent thereof, such claims should be understood to include incorporation of one or more such elements, neither requiring nor excluding two or more such elements.

We claim:

1. A needle-free injection device, comprising:
   a syringe assembly configured to draw in and expel injectable fluid, the syringe assembly being configured to expel injectable fluid upon application of pressurized gas to the syringe assembly from a gas reservoir; and
   a marking assembly configured to place a mark on or near an injection site to indicate an injection has occurred, the marking assembly being fluidly coupled within the needle-free injection device, such that the marking assembly is activated by post-injection venting of the pressurized gas of the needle-free injection device upon the conclusion of an injection sequence.

2. The needle-free injection device of claim 1, where the syringe assembly includes a slidable valve assembly configured to control buildup and release of pressure within the gas reservoir, the slidable valve assembly being progressively movable from a fired position to a stored position, where:
   when the slidable valve assembly is moved from the fired position to the stored position the slidable valve assembly fluidly couples the gas reservoir with the marking assembly.

3. The needle-free injection device of claim 1, where the marking assembly includes a housing adapted to retain a fluid reservoir.

4. The needle-free injection device of claim 3, where the fluid reservoir terminates in a nib adapted to draw fluid from within the fluid reservoir out of the fluid reservoir.

5. The needle-free injection device of claim 4, where a slidable valve assembly fluidly couples the gas reservoir with the housing such that exhaust gas from the gas reservoir is directed over a tip of the marking instrument.

6. The needle-free injection device of claim 4 wherein the housing terminates in an outlet through which the nib at least partially extends.

7. The needle-free injection device of claim 6 including a fluid pathway adapted to direct exhaust gas from the syringe assembly across the nib and out of the outlet.

8. A needle-free injection device comprising:
a user-grippable housing;
a syringe assembly movably secured to the housing and configured to expel injectable fluid out of a nozzle upon application of a pressurized gas to the syringe assembly;
a pressurized gas delivery mechanism disposed within the housing and configured to selectively the apply pressurized gas to the syringe assembly; and
a marking assembly configured to place a mark on or near an injection site to indicate an injection has occurred, the marking assembly being fluidly coupled with the pressurized gas delivery mechanism, such that the marking device is activated by post-injection exhaust gas from the pressurized gas delivery mechanism upon the conclusion of an injection sequence.

9. The needle-free injection device of claim 8 wherein the exhaust gas is directed to the marking assembly upon post-injection venting of the needle-free injection device.

10. The needle-free injection device of claim 8 wherein the marking assembly includes a housing configured to retain a fluid reservoir.

11. The needle-free injection device of claim 10 wherein the fluid reservoir is a marker having a nib.

12. The needle-free injection device of claim 11 wherein the exhaust gas is directed over the nib of the marker and onto a surface of an injection recipient.

13. A needle-free injection device, comprising:
a gas reservoir;
a syringe assembly configured to expel injectable fluid out of a nozzle upon application of pressurized gas from the gas reservoir to the syringe assembly;
a pressurized gas delivery mechanism adapted to apply pressurized gas to the syringe assembly;
a marking assembly configured to place a mark on or near an injection site to indicate an injection has occurred; and
an exhaust gas pathway configured to direct at least a portion of post-injection exhaust gas from the pressurized gas delivery mechanism to activate the marking assembly upon the conclusion of an injection sequence.

14. A needle-free injection device comprising:
a syringe assembly configured to expel injectable fluid upon application of a pressurized gas to the syringe assembly;
a pressurized gas delivery mechanism configured to selectively apply pressurized gas to the syringe assembly; and
a marking assembly configured to place a mark on or near an injection site to indicate an injection has occurred, the marking assembly being fluidly coupled with the gas delivery mechanism, such that the marking assembly is activated by post-injection venting of the gas delivery mechanism upon the conclusion of an injection sequence.

15. The needle-free injection device of claim 14 wherein the marking assembly includes a housing configured to retain a fluid reservoir.

16. The needle-free injection device of claim 15, where the fluid reservoir terminates in a nib adapted to draw fluid from within the fluid reservoir out of the fluid reservoir.

17. The needle-free injection device of claim 16 wherein exhaust gas from the post-injection venting of the gas delivery mechanism is directed over the nib and onto a surface of an injection recipient.

18. The needle-free injection device of claim 14 wherein the syringe assembly includes a slidable valve assembly configured to control buildup and release of pressurized gas.

19. The needle-free injection device of claim 18 wherein the slidable valve assembly is progressively movable from a fired position to a stored position, thereby fluidly coupling the marking assembly with the pressurized gas delivery mechanism.

20. The needle-free injection device of claim 19 wherein the marking assembly is fluidly coupled with the gas delivery mechanism by an air passage configured to direct airflow of post-injection exhaust gas to the marking assembly.

* * * * *